United States Patent [19]
Hök

[11] Patent Number: 5,509,414
[45] Date of Patent: Apr. 23, 1996

US005509414A

[54] APPARATUS AND METHOD FOR NON-CONTACTING DETECTION OF RESPIRATION

[75] Inventor: Bertil Hök, Västerås, Sweden

[73] Assignee: Hök Instrument AB, Vasterås, Sweden

[21] Appl. No.: 312,756

[22] Filed: Sep. 27, 1994

[51] Int. Cl.⁶ .................................. A61B 8/00; A61B 5/08
[52] U.S. Cl. ......................... 128/660.02; 128/721
[58] Field of Search ..................... 128/660.01, 660.02, 128/662.03, 662.04, 721, 725

[56] References Cited

U.S. PATENT DOCUMENTS

| | | | |
|---|---|---|---|
| 3,777,740 | 12/1973 | Hokanson | 128/661.08 |
| 4,122,427 | 10/1978 | Karsh | 128/661.07 |
| 4,197,856 | 4/1980 | Northrop | 128/661.07 |
| 5,220,922 | 6/1993 | Barany | 128/661.07 |

OTHER PUBLICATIONS

Ogura et al "Respiration Flowmeter" International (European) Appln Publ. No. 0 051 293 published Dec. 5, 1982.

Plant D. et al "Design & Construction of UTS Pneumotachometer", IEEE BME Trans. vol. BME–77 No. 10 Oct. 1980.

Blumenfeld, W et al "A Coaxial UTS Pneumotachometer", Med & Biol Eng. v 13, No. 6 pp. 855–860, Nov. 1975.

*Primary Examiner*—Francis Jaworski
*Attorney, Agent, or Firm*—Watson, Cole, Grindle & Watson

[57] ABSTRACT

Apparatus and method for detecting air flow at the mouth and nose of a subject, including a transducer for converting electrical signals into ultrasound waves and vice versa, means for directing the ultrasound waves toward the mouth and nose of the subject and receiving return waves, and a detector to analyze electrical signals converted by the transducer from the return ultrasound waves.

18 Claims, 2 Drawing Sheets

APPARATUS AND METHOD FOR NON-CONTACTING DETECTION OF RESPIRATION

BACKGROUND OF THE INVENTION

The respiratory system constitutes a vital function of most animals, including man. Therefore, it is an important objective in health care to control this function. This includes assessment of the respiratory rhythm and intensity. Normally, in patients breathing spontaneously, this assessment is performed by human observation and a stop-watch, using three of the natural senses: hearing (the respiratory sounds), vision (abdominal movements), and tactile sensing (the flow of warm, and moist air out of the mouth and nose of the subject).

Human observation is not practical in all situations, for example, due to limited access to the subject, or limited availability of personnel. Life-threatening respiratory depression and/or apnea can occur suddenly, after long periods of normal respiratory function. Complications can be either obstructive, i.e., caused by partial or complete blockage of the airways, or due to insufficiencies in the central respiratory control system, or a combination of both. The sleep apnea syndrome is an example of the former, whereas the latter can occur after use of morphine or other pain-relieving substances. The etiology of the sudden infant death syndrome, striking mostly newborns, is still controversial, but seems to be related to insufficient respiratory control.

Consequently, there is a need for automated respiratory monitoring of these and other groups of patients. This need is well recognized; and a number of devices have been reported. The simplest approach is to detect the abdominal movements, by impedance measurement, pressure variations in a mattress, or by measuring the circumference of belts or straps placed around the chest. These detectors, however, have the serious error of dubious response to obstructive respiratory disorder. If an obstructive apnea occurs, the subject is usually still making efforts to breathe, and the movement detectors have difficulties in discriminating between a successful effort or one that is not.

A more successful approach is to detect the flow of air at the mouth and nose region of a subject. This can be done using small thermistors, or by measuring small pressure variations, or acoustic noise generated by the flow. However, placing sensors in this region is not comfortable for the patient, and involuntary displacement of them may cause false alarms, since this condition is normally misinterpreted as an apnea.

SUMMARY OF THE INVENTION

The objective of the present invention is to detect the flow of air at the mouth and nose of a subject without physical contact. The invention makes use of the well-known fact that the velocity of sound waves is influenced by air flow. Thus by measuring the velocity of sound it is, in principle, possible to detect respiratory flow, provided that access to this information can be made without disturbing influences from other sources. The device must not only be sensitive to respiratory air flow, but also specific to this entity.

Major difficulties are to provide signal access without physical contacting means and to avoid sensitivity to body movements of the subject. A possible, yet unsatisfactory solution is to let an ultrasound wave pass alongside the mouth and nose region, and measure the transit time of wave propagation in the air of this region. The turbulent flow of air at expiration will then cause fluctuations of the transit time. However, this requires that a transmitter and a receiver be located close to the head of the subject, and this arrangement will easily become displaced, thus losing its sensitivity, due to head movements.

The large difference in acoustic impedance between body tissues and air makes the body surface an almost perfect reflector of acoustic waves. Ideally, one would like to direct a wave of ultrasound to the mouth and nose region of the subject, and then extract the information on the eventually expired air flow from the reflected wave. This is not easily done, since again head movements will cause variations in both the transit time and the intensity of the reflected wave that are much larger than the small variation due to air flow.

From the point of view of basic physics, wave reflection is a reciprocal process, i.e., reversal of the propagation direction will reproduce exactly the same wave pattern. By moving his/her head, the subject will cause exactly equal change of reflectance in two waves of arbitrary shape, travelling the same path but in opposite directions. Contrary to this behavior, the variation of velocity of sound due to air flow is nonreciprocal. If the original sound wave is speeded up by the air flow, the reversed wave will be correspondingly delayed. The recognition of this difference, as far as reciprocity is concerned, between the desired entity (air flow from breathing subject) and the undesired (movements of the subject), is the core of the present invention.

Devices making use of the distinction between reciprocal and non reciprocal effects are known in optics, and were demonstrated by the French physicist G. Sagnac in 1913. They are basic to laser and fiberoptic gyroscopes, with extensive use of aeronavigation. Corresponding devices operating on acoustic waves (either audible or ultrasonic) can be designed somewhat differently, partly due to the slower velocity of sound compared to light, and partly due to the fact that linear, and phase sensitive detection is feasible. Diffraction is frequently an unwanted phenomenon that is more difficult to handle in the acoustic domain, due to the longer wavelengths.

BRIEF DESCRIPTION OF THE DRAWINGS

The characteristics of the present invention are described more specifically in the following detailed description of preferred embodiments of my invention, which are described with reference to illustrations in the accompanying drawings, in which.

DETAILED DESCRIPTION OF THE PREFERRED EMBODIMENT

Figure 1:
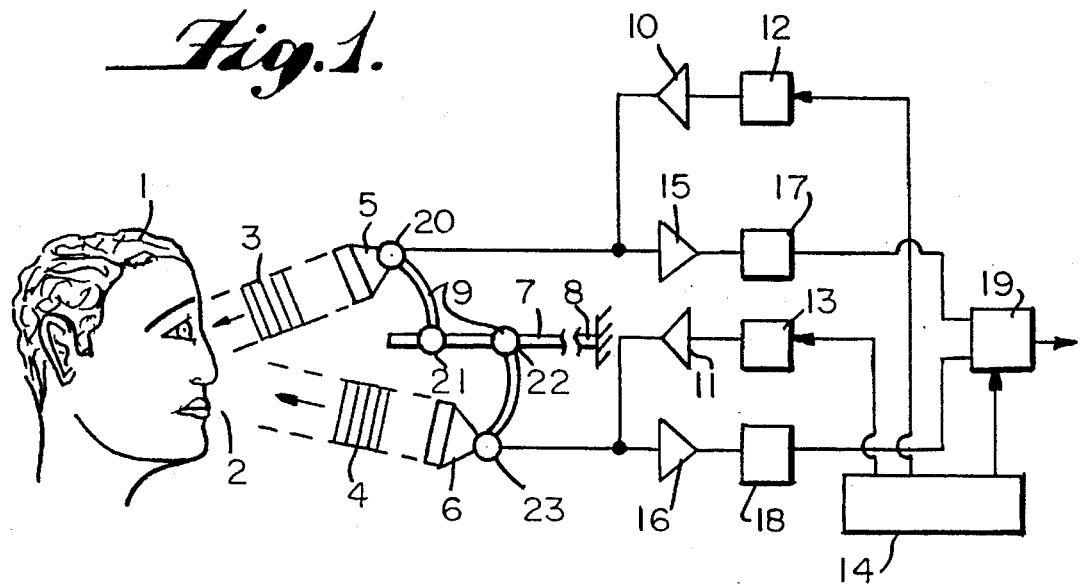
FIG. 1 is a diagrammatic representation of one embodiment of the invention.

FIG. 1 diagrammatically illustrates one embodiment of my invention. Two ultrasound waves 3 and 4 are impinging on the mouth and nose region 2 of a subject 1. The waves are emitted by two transducers 5 and 6, which are connected to drive circuits, consisting of amplifiers 10, 11, waveform generators 12, 13, and control circuitry 14. The drive circuitry provides the transducers 5 and 6 with electrical impulses, in order to generate the desired wave patterns. The waves are directional, with one main propagation direction, and a given divergence with respect to this direction. Typically, the ultrasound waves have a frequency of 100 kHz, and a divergence of 5°. In the embodiment of FIG. 1, the ultrasound waves 3 and 4 have a short duration, about 5–10 cycles at the operating frequency. The output of the drive circuitry is adjusted so that the two transducers generate coincidental waveforms of approximately equal amplitude, frequency, phase and duration. The transducers 5 and 6 are oriented towards the mouth and nose region by directional means, for example, consisting of an arm structure 7, 8 and 9, which is fixed against the subject's bed at one end 8, whereas the other, head end 9, supports the transducers 5 and 6, positioned adjustably by joints 20, 21, 22 and 23 in a conventional manner.

The transducers are preferably of the piezoelectric or electrostatic type enabling conversion from electric voltage into ultrasound, and vice versa. Thus each transducer can operate both as a transmitter and as a receiver of ultrasound. When operating as a receiver, the drive voltage is switched off, and the transducer output voltage is monitored, using elements for signal analysis. Such elements are amplifiers 15 and 16, electronic filters 17 and 18, and a correlator element 19. The latter consists, in its simplest form, of analog comparators, converting the analog signals from the filters 17 and 18, into switching waveforms and logical function elements to provide a pulse, the length of which is defined by the timing differences between the leading edges of two received ultrasound waves.

The ultrasound waves 3 and 4 are reflected and scattered at the mouth and nose region 2 of the subject. The wave 3 will be partly reflected and received at transducer 6, and due to the reciprocity principle, a wave originally emitted from transducer 6 having equal characteristics will be received at transducer 5. The waveforms at the receiver ends will be dispersed compared to the emitted pulse, due to the irregular shape of the reflecting object.

In addition to these signal paths, waves 3 and 4 will also be reflected directly back to transducers 5 and 6, respectively. Therefore, in order to avoid possible confusion at the receiver end, transducers 5 and 6 should be separated by a distance, at least 20 cm, corresponding to the maximum dispersion caused by reflection against the subject, in the direction of wave propagation. This avoids the problem of possible interferences between the directly reflected waves and the waves passing the desired path from transducer 5 via the subject 1 to transducer 6, and those from transducer 6 to subject 1 to transducer 5.

Figure 2:
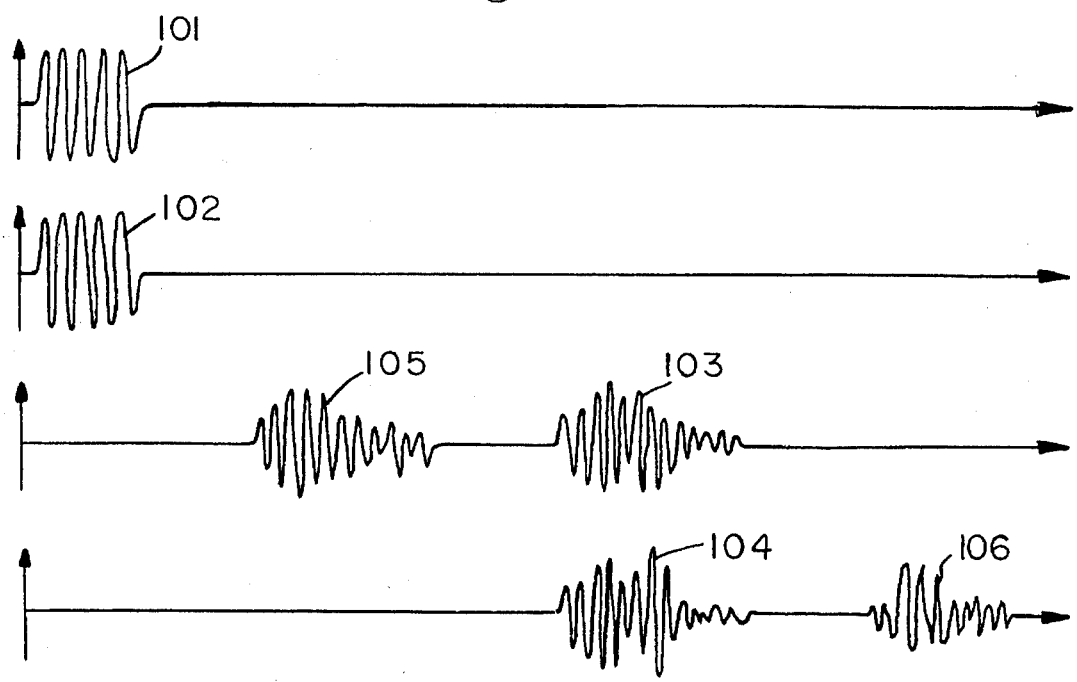
FIG. 2 shows schematic diagrams of waveforms used in the invention.

This is explained in more detail in relation to FIG. 2, schematically illustrating waveforms. The two upper diagrams show the waveforms 101 and 102 as they would appear if a detector transducer recorded them directly after launching. The two lower diagrams show the waveforms received by transducers 5 and 6, respectively. The waves 103 and 104, having travelled via the subject to the opposite transducer, arrive almost coincidentally, whereas the direct reflection 105 from and to transducer 5 arrives earlier due to the short distance between transducer 5 and the subject. The direct reflection 106 will arrive at transducer 6 considerably later, due to the longer distance between transducer 6 and the subject.

If the air is still, both waves reflected to opposite transducers appear at a time $t_O=(L_1+L_2)/c_0$, where $c_O$ is the velocity of sound in air (340 m/s at room temperature), and $L_1$ and $L_2$ are the distances between the subject and transducers 5 and 6, respectively. If the subject is expiring air, giving a net contribution to the velocity v in the direction of the ultrasound wave, the sound velocity will change to $c=c_0+v$, and the transit time to $t=L_1+L_2/c$. At a particular moment, v will add to $c_O$ in one of the waves, and subtract in the other, corresponding to $t+=(L_1+L_2)/(c_0+v)$, and $t-=(L_1+L_2)/(c_0-v)$. In the first order of approximation, the relative "differential" transit time variation is given by $(t+-t-)/t_0=2v/c_O$. Normal values of v are 0.1–1 m/s in subject at rest; thus the relative variation in the transit time will only be a fraction of a percent. If $L_1+L_2$ is 100 cm, and v= 0.1 m/s, then $t_0$=2.9 msec, and $(t_+-t_-)$=1.7 microsec. Timing variations of this order of magnitude can be readily measured, using standard circuit design elements.

It should be noted that the arrangement shown in FIG. 1 also applies to the case where the waves 3 and 4 are co-linear, with transducers 5, 6 directed towards one another. Then, reflections against the subject need not take place; still, non-reciprocal variations in the speed of sound along the path will be detected. This geometry has the disadvantage that the transducers must be positioned on each side of the subject's head. Thus it is only applicable in the supine position.

A more accurate, but also more complex embodiment of the correlator 19 performs the cross correlation algorithm on the entire waveforms 103 and 104. By quantitative and accurate measurement of $(t_+-t_-)$, an estimation of the intensity of each breath is provided, and it can even be used to provide an estimate of the tidal volume, based on an integration of this parameter over one breathing cycle.

Figure 3:
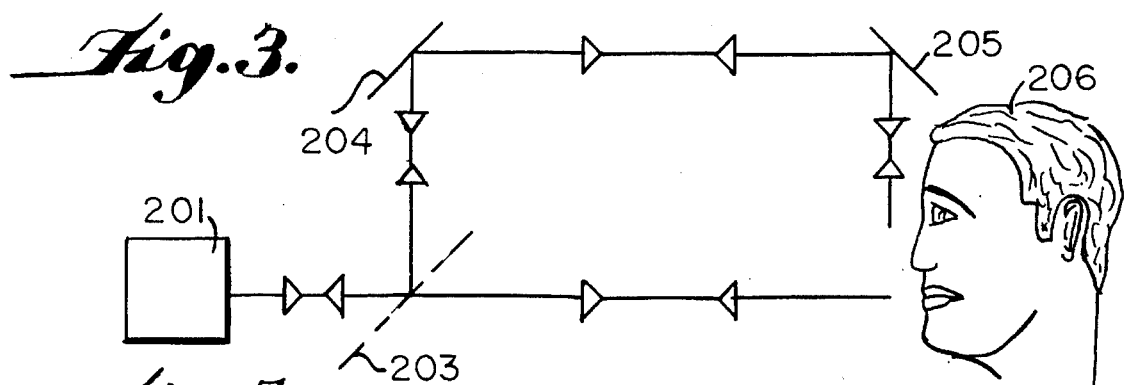
FIGS. 3 and 4A, 4B and 4C show alternative embodiments, the one in FIG. 4B being the preferred in terms of commercial realization.

FIG. 3 shows another embodiment of the invention. A transducer 201 emits an ultrasound beam 202. The beam passes a beamsplitter 203, which consists of a perforated sheet with an angle of incidence differing from 90°. The beamsplitter 204 causes the beam to propagate in a loop, both clockwise, and counterclockwise. The loop is defined by mirrors 204, 205 and an additional reflector, consisting of the subject 206, whose respiration is to be detected. The beamsplitter 203 also acts as exit port from the loop, and the waveforms are detected by the transducer 201 after travelling around the loop. Compared with the arrangement of FIG. 1, this interferometer design has the advantage of requiring only one transducer. It eliminates the need for matching the properties of the emitted waveforms, and its components, reflectors and beamsplitters, are non-expensive. On the other hand, in order to measure the differential transit time from the signal received in one single transducer, the ultrasound waves must have a shorter duration, and a smaller divergence than the configuration in FIG. 1, due to the longer transmission paths.

In FIG. 4 A, another embodiment of the invention is shown. Like the one illustrated by FIG. 1, the subject 303 is exposed to ultrasound waves from two transducers 301 and 302. In this case, the transducers emit continuous waves with slightly differing frequency. Typically, the transducers operate at 40 kHz, with a frequency difference of only 100 Hz. This small difference in frequency means that diffraction, and other wavelength dependent properties of the waves, are essentially the same. The separation in frequency is, however, large enough for the signals to be detected separately by the transducers 304 and 305, which are located closely to the emitting transducers 301,302, respectively. By tuning the receiver transducer to the opposite emitter, it is possible to exclude the effects of direct reflections. The routes of the ultrasound waves 306 and 307 are approximately identical, apart from a small parallax error due to the displaced positions of the transducer pairs. Narrow band detection is possible, using the standard techniques of synchronous, or lock-in amplifiers. The output of the synchronous amplifier is sharply low pass filtered with an upper frequency limit less than the frequency difference between the ultrasound waves in order to suppress the directly reflected signal. The circuit constitutes a type of phase detector which is well-known in the literature. The outputs of the phase detectors are connected to the input of a differential amplifier, the output of which is proportional to the phase difference between the two ultrasound waves. The respiratory air flow gives rise to a differential phase shift between the opposite waves, analogous to the differences in transit time derived above, whereas phase-shifts induced by movements of the subject's head occur simultaneously, and with equal sign, in both detectors. A difference in transit time of 1.7 microsec corresponds to a difference in phase of 24° at 40 kHz. The resolution of a well-designed phase detector is at least two orders of magnitude higher.

Figure 4A:
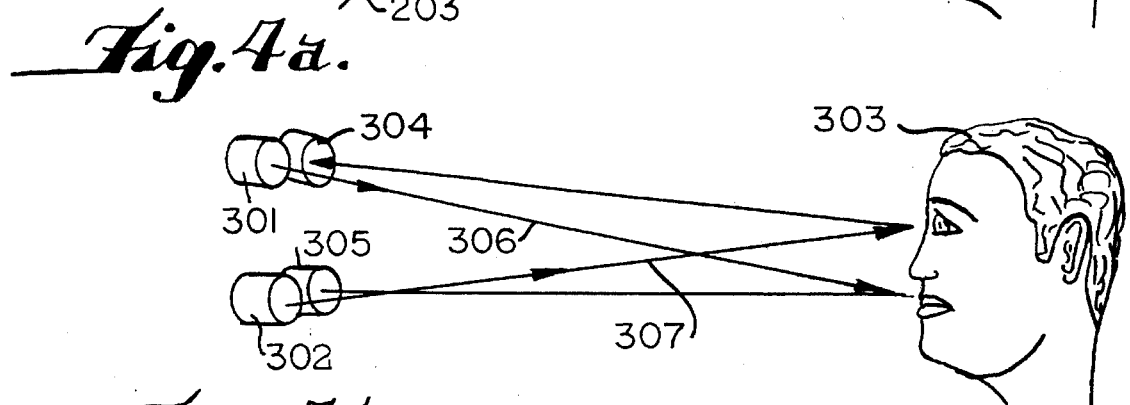
Figure 4B:
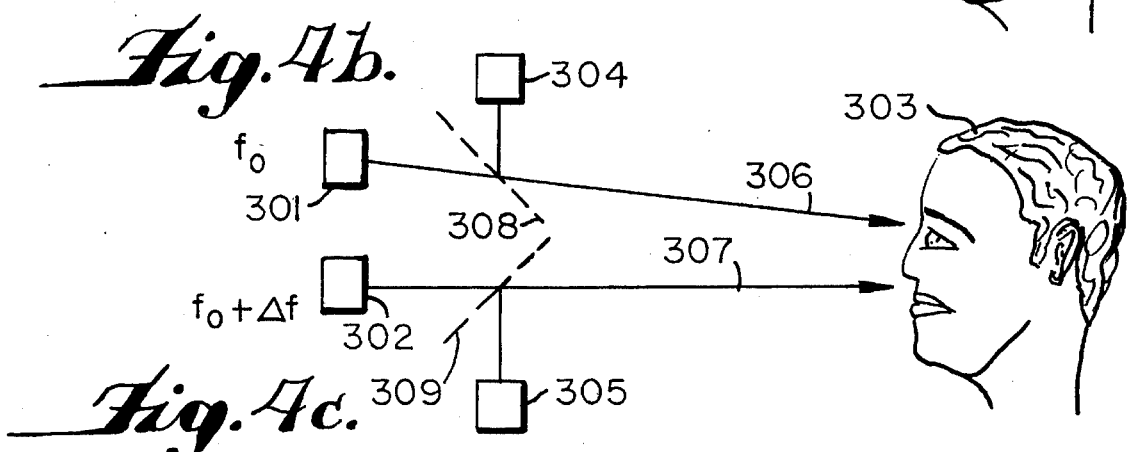

The embodiment in FIG. 4 A has the advantage that low-cost piezoelectric transducers can be used. Several manufacturers of low-cost transducers, e.g., Polaroid Corporation, Atlanta, USA, and Matsushita Electric Corp., Osaka, Japan, are available. These transducers can generally not be used in the designs based on pulsed waves, due to the high demand on short duration. On the other hand, the parallax error could be detrimental, making the system more sensitive to the subject's movements. The parallax error is removed in the embodiment shown in FIG. 4B, which is identical to the one shown in FIG. 4A, except for two beamsplitters 308, 309, which have been introduced to ensure that the two beams 306 and 307 will pass identical, but opposite routes.

The embodiment in FIG. 4B is preferred in terms of practical realizations, not only because it constitutes the less expensive solution, but because the positioning of the transducers is less critical, since the influence from the directly reflected wave is eliminated electronically by the small frequency difference, rather than by the physical design of the directional means, i.e., the arm structure 7, 8, 9 in FIG. 1, which needs to ensure that a path difference of at least 20 cm prevails.

Figure 4C:
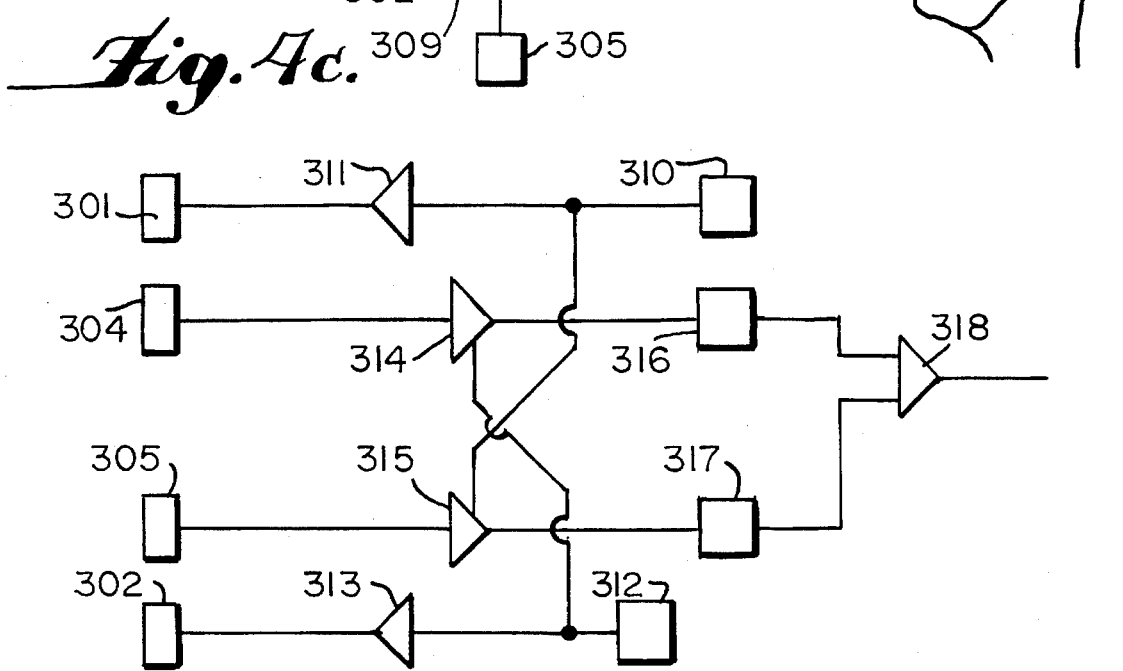

FIG. 4C shows, in more detail, the electronic circuitry used for the design outlined in FIG. 4A and B. An oscillator 310 gives a sinusoidal output at 40 000 Hz, and this signal is amplified in the amplifier 311, the output of which is the driving voltage to transducer 302 at a frequency of 40 100 Hz is provided by a second oscillator 312, and the amplifier 313. The signal from the receiving transducer 304, located closely to transducer 301, is fed to a synchronous amplifier 314, controlled by the oscillator 312, and then passes a low-pass filter with an upper frequency limit lower than 100 Hz. The signal at this point is a function of the phase of the ultrasound signal emitted by transducer 302. Analogously, the signal from the receiving transducer 305, physically located close to transducer 302, is fed to a synchronous amplifier controlled by the oscillator 310, which after passing the low-pass filter 317 provides a signal which is a function of the phase of the ultrasound signal emitted by transducer 301. Finally, the outputs from the two low-pass filters 316, 317 are fed to a differential amplifier, thus providing an output signal which is a functional of the phase difference by the two ultrasound waves travelling in opposite directions.

It should be noted that the physical effect used in the present invention is distinctly different from the Doppler effect, which involves relative motion between the sound source or a scatterer on the one hand, and a receiver on the other. The invention is also distinctly different from well-known flow meter designs, using opposite acoustical routes with the objective of reducing the influence of temperature variations in the velocity of sound. It also differs from the Sagnac effect, which makes use of electromagnetic pulses.

While my invention has been described hereinbefore with reference to several specific embodiments thereof, I do not wish the scope of my invention to be limited to those embodiments, but to include such modifications and alterations thereof as will be obvious to those of skill in the art. My invention, therefore, should only be limited to the scope, including equivalents, of the following, appended claims.

I claim:

1. Apparatus for the detection of air flow at the mouth and nose of a subject without contacting the subject, comprising:
   at least one transducer for converting an alternating electrical voltage into directional ultrasound waves in air, and for converting airborne ultrasound waves into electrical signals,
   means for directing said ultrasound waves through unconfined air from said at least one transducer towards the mouth and nose of said subject for reflection therefrom, said waves after or before reflection having their velocity non-reciprocally altered by air flow from respiration of said subject independently of physical movement of said subject,
   driving circuit means providing said at least one transducer with alternating voltage, and
   detector circuit means performing analysis of said electrical signals converted by said at least one transducer from said ultrasound waves after said waves are reflected by the mouth and nose of said subject, said analysis being directed to a determination of whether said reflected sound waves have had their velocity altered by air flow accompanying respiration of said subject.

2. Apparatus according to claim 1, wherein said at least one transducer and said directing means provide that one or more routes of said ultrasound waves are shared by two waves travelling in opposite directions.

3. Apparatus according to claim 2, wherein said ultrasound waves travelling in opposite directions are continuous and of different frequencies.

4. Apparatus according to claim 3, wherein said detector circuit means include at least two synchronous amplifiers operating in synchronism with each of said different frequencies.

5. Apparatus according to claim 2, wherein said ultrasound waves travelling in opposite directions are reflected by the mouth or nose of the subject.

6. Apparatus according to claim 1, wherein said detector circuit means includes at least one differential phase detector, the output of which corresponds to the difference in transit time between said ultrasound waves.

7. Apparatus according to claim 1, wherein said directing means includes a flexible arm extending from a fixed support to a head containing said at least one transducer, said arm having at least two adjustable joints.

8. Apparatus according to claim 1, wherein said detector circuit means includes at least two trigger circuits for providing an output signal corresponding to the difference in transit time of said ultrasound waves.

9. Apparatus according to claim 1, wherein said directing means comprises at least one beam splitter to define routes for said ultrasound waves.

10. Apparatus according to claim 1, wherein said alternating voltage is continuous.

11. Apparatus according to claim 1, wherein said alternating voltage is pulsed.

12. Apparatus for the detection of air flow at the mouth and nose of a subject without contacting the subject, comprising:

at least two transducers for converting an alternating electrical voltage into directional ultrasound waves in air, and for converting airborne ultrasound waves into electrical signals, means for directing said ultrasound waves through unconfined air from each of said at least two transducers toward the mouth and nose of said subject for reflection therefrom, said waves after or before reflection having their velocity non-reciprocally altered by air flow from respiration of said subject independently of physical movement of said subject, driving circuit means providing said at least two transducers with alternating voltage, and detector circuit means performing analysis of said electrical signals converted by said at least two transducers from said ultrasound waves after said waves are reflected by the mouth and nose of said subject, said analysis being directed to a determination of whether said reflected sound waves have had their velocity altered by air flow accompanying respiration of said subject.

13. Apparatus according to claim 12, in which said at least two transducers separated from said mouth and nose of said subject by lengths differing from each other by more than 20 cm.

14. Apparatus according to claim 12, wherein said alternating voltage is continuous.

15. Apparatus according to claim 12, wherein said alternating voltage is pulsed.

16. A method for detecting whether a subject is breathing and, if so, the relative force thereof without contacting the subject, comprising:

positioning a transducer for converting an alternating electrical voltage into directional ultrasound waves at the region of the mouth and nose of the subject, providing said transducer with alternating voltage to generate airborne ultrasound waves by said transducer, directing the ultrasound waves from said transducer through unconfined air toward the mouth and nose of the subject for reflection therefrom, said waves after or before reflection having their velocity non-reciprocally altered by air flow from respiration of said subject independently of physical movement of said subject, detecting ultrasound waves reflected to said transducer from said nose and mouth of said subject by converting said returning ultrasound waves into electrical signals, and analyzing said electrical signals to determine whether said reflected sound waves have had their velocity altered by air flow accompanying respiration of said subject.

17. Apparatus according to claim 16, wherein said alternating voltage is continuous.

18. A method according to claim 16, wherein said alternating voltage is pulsed.

* * * * *